United States Patent [19]

Montgomery et al.

[11] Patent Number: 4,576,817

[45] Date of Patent: Mar. 18, 1986

[54] ENZYMATIC BANDAGES AND PADS

[75] Inventors: Robert E. Montgomery, Pacific Palisades; Michael A. Pellico, Los Angeles, both of Calif.

[73] Assignee: Laclede Professional Products, Inc., Gardena, Calif.

[21] Appl. No.: 618,071

[22] Filed: Jun. 7, 1984

[51] Int. Cl.[4] ............................................. A61K 37/48
[52] U.S. Cl. ...................................... 424/94; 128/127; 128/156; 424/130; 435/25; 604/375; 604/904
[58] Field of Search .............. 604/289, 369, 375, 904; 424/14, 94, 130; 128/127, 130, 156; 435/25

[56] References Cited

U.S. PATENT DOCUMENTS

| | | | |
|---|---|---|---|
| 4,031,202 | 6/1977 | Laughlin et al. | 128/130 X |
| 4,122,158 | 10/1978 | Schmitt | 424/94 X |
| 4,150,113 | 4/1979 | Hoogendoorn et al. | 424/50 |
| 4,178,362 | 12/1979 | Hoogendoorn et al. | 424/94 X |
| 4,226,232 | 10/1980 | Spence | 128/156 |
| 4,269,822 | 5/1981 | Pellico et al. | 424/94 X |
| 4,379,141 | 4/1983 | Hasegawa et al. | 424/94 |
| 4,476,108 | 10/1984 | Kessler et al. | 424/130 X |
| 4,486,408 | 12/1984 | Kiel | 424/94 |
| 4,537,764 | 8/1985 | Pellico et al. | 424/94 X |

FOREIGN PATENT DOCUMENTS 2488797  2/1982  France ................................ 424/94

*Primary Examiner*—Helen M. McCarthy
*Attorney, Agent, or Firm*—Donald Diamond

[57] ABSTRACT

Enzymatic absorbent materials such as bandages and pads, for body contact applications, contain serum-activated oxidoreductase enzyme for producing hydrogen peroxide upon contact of the enzymatic materials with serum. An illustrative serum-activated oxidoreductase enzyme is glucose oxidase with the corresponding substrate in serum being glucose.

20 Claims, No Drawings

ENZYMATIC BANDAGES AND PADS

BACKGROUND OF THE INVENTION

This invention relates to absorbent materials adapted for use in body contact applications and, more particularly, to enzymatic absorbent materials such as bandages and pads that produce a bacteriostatic effect upon contact with body fluids such as serum.

Absorbent materials in the form of bandages and pads have long been employed in body contact applications where coverage and protection of a wound and absorption of its fluids are desirable. Bandaging can serve to physically protect an open wound from the surrounding environment, which is often replete with harmful bacteria, and to absorb fluid materials such as pus, blood and serum to thereby promote the healing of the wound. Accordingly, bandages are constructed of strong, yet absorbent, materials such that retention of extraneous fluids can be accomplished without a concomitant loss of strength.

Absorbent materials such as woven fibers, porous foam pads, absorbent membranes and solvent-based porous elastomers have been utilized in the manufacture of bandages and pads. A wide of variety of raw materials have been employed in an attempt to obtain physically occlusive structures that retain their strength when soaked with fluid from an open or weeping wound or other body fluid source. Materials such as cellulose and its derivatives (cellulosics), polyester, nylon, polyacrylamide, collagen, polyurethane and polyvinyl alcohol have been fabricated into structures such as woven fibers, foam pads, porous membranes, elastomers and multi-layered combinations of the aforementioned structures. Regardless of the material used, all bandages and pads employed in the protection of open wounds must satisfy the requirement of good absorbency in order to be effective.

An absorbent material in contact with an open or weeping wound will retain a substantial amount of blood, blood serum, pus and a variety of wound exudates. Bandages are often constructed in such a way that moisture retained by the absorbent material in contact with the wound will transpire through the side of the bandage opposite to that of the source of the fluids, i.e., the open wound. Although structures such as these tend to decrease the amount of moisture retained by the absorbent material, other exudates such as white blood cells, bacteria, eletrolytes, and red blood cells are retained. These exudates accumulate as a function of the amount of time an absorbent material is in contact with an open or weeping wound.

As a result of the retention of such a wide variety of biological substances, a moist absorbent structure can become an effective breeding ground for potentially harmful bacteria. Such an absorbent structure in contact with body fluid of the type mentioned above can be characterized as a culture support medium that can give rise to a large number of potentially harmful bacterial colonies in a relatively small volume. Since the accumulated bacteria and their waste products remain in contact with the open or weeping wound, they can leach out of the absorbent structure and back to the body. In this connection, symptoms classifiable as toxic shock syndrome have been associated with the use of certain types of feminine hygiene tampons, i.e., internally disposed feminine hygiene absorbent pads.

It would, of course, be advantageous to provide absorbent materials in the form of bandages, pads, strings and the like that would inhibit bacterial growth in body fluids which are absorbed by or otherwise associated with such absorbent materials or structures.

It is disclosed in the prior art that polymeric wound dressings for burns may include antibacterial agents, antibiotics, antifungal agents, proteolytic enzymes as well as local anesthetics, hormonal compounds and lubricating and barrier chemicals. See, for example, U.S. Pat. No. 4,122,158 (Schmitt, 1978) and U.S. Pat. No. 4,226,232 (Spence, 1980).

It is also disclosed in the prior art that enzymatic agents can be incorporated into oral products such as toothpaste and chewing gum for producing hydrogen peroxide during oral use.

U.S. Pat. No. 4,150,113 (Hoogendoorn et al., 1979) and U.S. Pat. No. 4,178,362 (Hoogendoorn et al., 1979) disclose, respectively, an enzymatic toothpaste and an enzymatic chewable dentifrice containing glucose oxidase which acts on glucose present in saliva and tooth plaque to produce hydrogen peroxide. The patentees note that oral bacteria, through enzymes systems having SH-GROUPS, effect glycolysis of food products containing sugars and point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

SUMMARY OF THE INVENTION

In accordance with one aspect of this invention, there is provided enzymatic absorbent material for body contact application containing, per gram of material, from about 1.0 to about 1,000 International Units of serum-activated oxidoreductase enzyme for producing hydrogen peroxide upon contact of said material with serum.

In accordance with a second aspect of this invention, there is provided enzymatic absorbent fiber for conversion into enzymatic absorbent material that is adapted for body contact application, wherein the fiber contains, per gram of fiber, from about 1.0 to about 1,000 International Units of serum-activated oxidoreductase enzyme for producing hydrogen peroxide upon contact with serum.

DETAILED DESCRIPTION

The enzymatic absorbent materials of this invention comprise fluid absorbent structures that incorporate serum-activated oxidoreductase enzyme for producing hydrogen peroxide upon contact with serum. Fluid absorbent structures, in the form of bandages, pads, strips and the like, can be prepared from precursors and by processes well-known in the art to provide appropriate designs and configurations that are adapted for particular body contact applications. Structural precursors such as woven fibers, porous foam pads, absorbent membranes and solvent-based porous elastomers can be utilized in the manufacture of the fluid absorbent structures. Gauze bandaging alone or secured to adhesive strip and feminine hygiene absorbent pads and tampons, as well as other externally and internally utilizable body contact devices having high absorbency characteristics, can be advantageously utilized in the practice of this invention.

The enzymatic absorbent material of this invention, which incorporates oxidoreductase enzyme, is adapted to be used in body contact applications that encounter body fluids. These fluids, including blood and tissue serum, contain oxidizable substrate and other ingredients which undergo an enzymatic reaction in the presence of oxidoreductase enzyme specific to the substrate to produce hydrogen peroxide. Oxidoreductase enzymes which can be utilized in the practice of this invention and the corresponding oxidizable substrates in serum are set forth in the following table:

TABLE A

| OXIDOREDUCTASE ENZYME | OXIDIZABLE SUBSTRATE |
| --- | --- |
| Glucose Oxidase | B—D-glucose |
| Hexose Oxidase | Hexose |
| Cholesterol Oxidase | Cholesterol |
| Galactose Oxidase | D-galactose |
| Pyranose Oxidase | Pyranose |
| Choline Oxidase | Choline |
| Pyruvate Oxidase | Pyruvate |
| Oxalate Oxidase | Oxalate |
| Glycollate Oxidase | Glycollate |
| D-aminoacid Oxidase | D-aminoacid |

In an illustrative enzymatic reaction, glucose oxidase in the enzymatic absorbent material catalyzes the interaction of Beta-D-glucose, water and oxygen in the serum to produce hydrogen peroxide and gluconic acid.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

The oxidoreductase enzyme is generally present in the enzymatic absorbent material in an amount from about 1.0 to about 1,000 International Units (hereinafter sometimes abbreviated as IU) per gram of material and, preferably, in an amount from about 10 to about 500 IU per gram of material. The term International Unit(s) identifies that amount of enzyme that will effect catalysis of 1.0 micromole of substrate per minute at pH 7.0 and 25° C. Oxidoreductase enzymes are supplied in dry or liquid form with the label specifying the concentration in International Units on a per gram or per milliliter basis, as appropriate.

In addition to the oxidoreductase enzyme for producing hydrogen peroxide, the enzymatic material can be provided with a second enzyme, namely, a peroxidatic peroxidase for interacting with hydrogen peroxide and an oxygen-accepting anion in serum for producing an oxidized anionic bacterial inhibitor. Peroxidases which can be used in the practice of this invention include lactoperoxidase, horseradish peroxidase, iodide peroxidase, chloride peroxidase and myeloperoxidase. The peroxidase is generally present in the enzymatic absorbent material in an amount from about 0.1 to about 10,000 International Units per gram of material, and, preferably, in an amount from about 10 to about 500 International Units per gram of material.

Oxygen-accepting anions in serum include thiocyanate, chloride and iodide ions which, in the presence of hydrogen peroxide and peroxidase, are oxidized to hypothiocyante, hypochlorite and hypoiodite, respectively.

The enzymatic absorbent material described herein may be augmented by additionally incorporating into the material supplementary ingredients as, for example, (a) oxidizable substrate specific to the oxidoreductase enzyme utilized in the material, and (b) oxidizable salt such as the thiocyanate, chloride or iodide salt of sodium, potassium, ammonium, calcium or magnesium or mixtures of such salts.

The oxidizable substrate is generally present in the enzymatic absorbent material in an amount from about 0.015 to about 0.6 millimole per gram of material and, preferably, in an amount from about 0.025 to about 0.1 millimole per gram of material. The oxidizable salt is generally present in the enzymatic absorbent material in an amount from about 0.0001 to about 0.01 millimole per gram of material and, perferably, from about 0.001 to about 0.006 millimole per gram of material. The term millimole identifies that quantity in grams corresponding to the molecular weight of the composition divided by one thousand.

The operable integrity of the enzymatic system can be affected by catalase which is present in commercial glucose oxidase as well as mucous membrane tissue, blood and blood serum. Catalase, which is extraneous to the enzymatic system of this invention, competes with lactoperoxidase for hydrogen peroxide. In order to reduce loss of hydrogen peroxide through the presence of catalase, an effective amount of an enzymatic inhibitor specific to catalase can be advantageously incorporated into the enzymatic absorbent material. An ascorbic salt such as sodium ascorbate, potassium ascorbate, ascorbyl palmitate, or mixtures thereof can be used as an enzymatic inhibitor which is specific to catalase. An effective amount of ascorbate salt for catalase inhibition is from about 0.000001 to about 0.0001 millimole per gram of enzymatic absorbent material. Iron salts such as ferrous sulfate can be incorporated into the enzymatic absorbent material as a potentiator for ascorbate salt in its role as catalase inhibitor.

The enzymatic material of this invention may advantageously be formulated with an aminohexose as, for example, an aminoglucose such as glucosamine, N-acetyl glucosamine or mixtures thereof in order to increase the yield or accumulation of oxidized anionic bacterial inhibitor. The aminoglucose is generally present in the enzymatic material in an amount from about 0.0001 to about 0.002 millimole per gram of enzymatic material and, preferably, in an amount from about 0.003 to about 0.001 millimole per gram of enzymatic material.

In an alternative embodiment of this invention, the oxidoreductase enzyme can be incorporated into absorbent fibers of natural or synthetic materials for conversion into enzymatic bandages and pads.

The enzymes of this invention may be advantageously encapsulated to enhance storage stability in the enzymatic bandage or pad until utilization of the same. The encapsulating material can be composed of a water soluble polymer or a polymer permeable to a substrate specific to the enzyme or enzymes contained therein. An illustrative encapsulating material is carboxymethylcellulose.

The enzymatic absorbent materials can be prepared by various procedures including: (a) solution deposition of the oxidoreductase enzyme and optional ingredients onto the absorbent structure, (b) incorporation of the oxidoreductase enzyme into a spinning solution that is extruded as fiber filament which can be converted into bandages and pads, and (c) incorporation of the oxidoreductase enzyme into the chemical constituency which form polymeric foams and subsequent injection or solvent despostion of the aforementioned optional ingredients as well as other special purpose additives.

EXAMPLE I

This example illustrates the solution deposition of an oxidoreductase enzyme onto a spun cotton pad and the bacteriostatic effect of the resulting enzymatic pad.

An aqueous enzymatic solution was prepared by adding 0.2 gm of polyvinylpyrolidone (Mol. Wt. 250,000) and 1,000 IU of glucose oxidase (approx. 4.0 mg) to a vessel containing 10 ml of distilled water with stirring through the use of a magnetic stirring bar and electric stirrer. Low turbulence was maintained during stirring to avoid any impairment of the enzyme.

A spun cotton pad with dimensions of 3.0 cm by 3.0 cm by 1.0 cm was impregnated with 1.0 ml of the aqueous enzyme solution by applying the solution to the pad through a standard medicinal dropper. The residual water was allowed to evaporate from the pad at room temperature (25° C). The resulting pad and a non-enzymatic control pad were tested for bacteriostatic properties.

The enzymatic and non-enzymatic pads were placed in separate culture tubes, and approximately 10 ml of human blood serum was added to each of the culture tubes. The tubes were then innoculated with *Staphylococcus aureus* at a concentration level of $1.0 \times 10^5$ organisms per milliliter of serum and assayed for bacterial counts at the end of each 4-hour segment for 24 hours. Cultures to determine counts were prepared from tryptic soy agar and incubated at 35° C. for 48 hours under aerobic conditions. The results are set forth in the following table:

TABLE I

| Time, hr. | Glucose Oxidase Enzymatic Pad S. aureus Count/ml | Non-Enzymatic Pad S. aureus Count/ml |
| --- | --- | --- |
| 0 | $1.2 \times 10^5$ | $1.4 \times 10^5$ |
| 4 | $8.6 \times 10^4$ | $2.9 \times 10^5$ |
| 8 | $6.6 \times 10^4$ | $8.5 \times 10^5$ |
| 12 | $5.9 \times 10^4$ | $4.4 \times 10^6$ |
| 16 | $5.1 \times 10^4$ | $9.1 \times 10^6$ |
| 20 | $4.0 \times 10^4$ | $3.6 \times 10^7$ |
| 24 | $3.2 \times 10^4$ | $7.0 \times 10^7$ |

EXAMPLE II

This example illustrates the preparation of enzymatic fibers by incorporating oxidoreductase enzyme and peroxidatic peroxidase enzyme into a wet spinning solution that is extruded in fiber form. In addition, this example illustrates the bacteriostatic effect of the resulting enzymatic fiber.

To methylene dichloride contained in a 250 ml beaker, there was added 10 gm of celluose triacetate in pellet form to bring the total volume of the contents to 100 ml. An aqueous enzymatic solution having a volume of 15 ml was prepared by admixing glucose oxidase (500 IU/ml) and lactoperoxidase (500 IU/ml) with distilled water. The aqueous enzyme solution was added to and admixed with the cellulose triacetate solution for 30 minutes which resulted in an emulsion of the aqueous phase in the organic phase.

Fibers were formed from the enzymes/polymer emulsion by wet spinning technique. A 10 ml hypodermic syringe was filled with the emulsion. The syringe was used to extrude the emulsion through a No. 20 hypodermic needle into 100 ml of toluene that was contained in a 150 ml graduated cylinder.

During the extrusion process, the emulsion coagulated as a fiber in the form of ringlets about 2 cm in diameter which slowly settled to the bottom of the graduated cylinder. The rate of extrusion was controlled to provide a continuous fiber strand of the ringlets at a rate slow enough to prevent sticking at the bottom of the cylinder. Upon completion of the extrusion step, the fibers were removed from the toluene bath and air-dried before testing for bacteriostatic properties. Approximately 9.6 gm of fiber were obtained.

The fiber was assayed for activity in respect of both glucose oxidase and lactoperoxidase. An activity of 300 IU per gram of fiber was obtained for each enzyme.

A first control fiber was prepared by the foregoing extrusion procedure, except that the extrusion composition did not contain either glucose oxidase or lactoperoxidase. A second control fiber was prepared in accordance with the procedure used in the preparation of the first control fiber, except that the extrusion composition was modified to contain bovine serum albumin, a protein. Neither of the control fibers showed any enzyme activity in tests for either glucose oxidase or lactoperoxidase.

The fibers described above are of the type that are suitable for the manufacture of woven bandages.

The fibers were tested for bacteriostatic properties using *Staphylococcus aureus* (ATCC 653A) and *E. coli* (ATCC 25923). Each organism was inoculated into a 20 ml portion of tryptic soy broth and incubated at 35° C. for 24 hours. Each of the resulting cultures was washed with a phosphate buffer (pH 6.5 and 0.01 M) by centrifuging to obtain a suspension of cells, which was diluted 1:10.

Fresh human blood serum samples were prepared in 6 screw cap tubes that held 20 ml of serum in each. Twenty microliters of the diluted bacterial cell suspension were inoculated into each of the tubes containing serum. Thereafter, a 100 mg fiber sample was placed in each of the inoculated serum tubes which were incubated at 35° C. for the duration of the testing. Occasional manual agitation of the tubes was undertaken during the test period.

Bacterial counts of the samples were taken at the end of each 4-hour segment for 24 hours. Tryptic soy agar was used as the plating medium for each sample and the plates were incubated at 35° C. for 48 hours under aerobic conditions. The results are set forth in the following table:

TABLE II

| Time, hr. | S. aureus Count | E. coli Count/ml |
| --- | --- | --- |
| | 2A Enzymatic Fiber Glucose Oxidase & Lactoperoxidase | |
| 0 | $2.0 \times 10^5$ | $1.0 \times 10^5$ |
| 4 | $6.2 \times 10^3$ | $3.8 \times 10^4$ |
| 8 | $2.0 \times 10^3$ | $2.2 \times 10^4$ |
| 12 | $1.8 \times 10^3$ | $7.6 \times 10^3$ |
| 16 | <1,000 | $5.1 \times 10^3$ |

TABLE II-continued

| Time, hr. | S. aureus Count | E. coli Count/ml |
|---|---|---|
| 20 | <300 | $1.4 \times 10^3$ |
| 24 | <100 | <100 |
| 2B Non-Enzymatic Fiber | | |
| 0 | $2.0 \times 10^5$ | $1.0 \times 10^5$ |
| 4 | $6.6 \times 10^5$ | $9.5 \times 10^5$ |
| 8 | $2.1 \times 10^6$ | $5.1 \times 10^7$ |
| 12 | $8.8 \times 10^6$ | $4.9 \times 10^8$ |
| 16 | $2.2 \times 10^7$ | $1.0 \times 10^9$ |
| 20 | $3.7 \times 10^7$ | $1.1 \times 10^9$ |
| 24 | $5.0 \times 10^7$ | $1.6 \times 10^9$ |
| 2C Fiber/Bovine Serum Albumin | | |
| 0 | $2.0 \times 10^5$ | $1.0 \times 10^5$ |
| 4 | $4.5 \times 10^5$ | $9.5 \times 10^5$ |
| 8 | $9.9 \times 10^5$ | $5.3 \times 10^6$ |
| 12 | $6.1 \times 10^6$ | $8.9 \times 10^6$ |
| 16 | $8.4 \times 10^6$ | $1.2 \times 10^7$ |
| 20 | $1.0 \times 10^7$ | $8.6 \times 10^7$ |
| 24 | $4.2 \times 10^7$ | $2.1 \times 10^9$ |

EXAMPLE III

This example illustrates a method for incorporating oxidoreductase enzyme into yieldable, semi-rigid foam and the bacteriostatic properties of the resulting enzymatic foam.

An aqueous enzyme solution was prepared by admixing 1,000 IU of glucose oxidase (approx. 4.0 mg) with 40 ml of cold, distilled water, under moderate agitation, until the enzyme dissolved.

An isocyanate terminated, prepolymer solution was prepared by reacting stoichiometric amounts of 80/20 2,4-/2,8 tolylenediisocyanate and Carbowax 1,000 polyoxyethylene polyol (Mol. Wt. 1,000) at 135° C. for 5 hours in the presence of a catalyst comprising 2-ethylhexanoic acid and tin octoate. The resulting urethane prepolymer was diluted to 90% solids with acetone.

To 24.5 gm of the acetone solution of prepolymer, there was added 0.22 gm of Tween 80 (a polyoxyethylene derivative of sorbitan fatty acid ester having a molecular weight of about 1,309) and the viscous mixture was stirred by hand for approximately 30 seconds. Twenty milliliters of the aqueous enzyme solution was added to the prepolymer composition and the resulting paste-like mixture was stirred to obtain a dispersion of the ingredients. The remaining aqueous enzyme solution was then added to the reaction mixture which was again stirred to obtain dispersion of the ingredients. Upon completion of the enzyme addition and dispersion steps, the reacting mass was poured into a Petri dish (100 mm diameter) and allowed to remain at ambient temperature for 5 minutes at which time the reaction was substantially complete.

There was obtained from the reaction a white, spongy, wet, semi-rigid, enzymatic foam that was approximately 1.2 to 1.4 centimeters thick. The wet foam was removed from the dish and stored in a refrigerator at approximately 5° C., with the foam remaining damp during storage. One gram of this foam material (dry weight) was assayed for glucose oxidase activity using glucose as a substance, horseradish peroxidase and o-dianisidine as a chromogen. The activity of the one gram piece of foam was approximately 12 IU per gram, or about 60% of the original activity.

Five grams of enzymatic foam (dry weight) were placed in a large culture tube containing 10 ml of whole pig's blood. The blood was inoculated with approximately 200,000 organisms of S. aureus. A control tube was prepared by placing 5 grams of non-enzymatic foam in a culture tube containing 10 ml of whole pig's blood which was inoculated with approximately 200,000 organisms of S. aureus. Bacterial counts, per one ml of blood, were taken at the end of each 4-hour segment for 24 hours. The results are set forth in the following table:

TABLE III

| Time, hr. | Glucose Oxidase Enzymatic Foam S. aureus Count | Non-Enzymatic Foam E. coli Count/ml |
|---|---|---|
| 0 | $2.0 \times 10^5$ | $2.0 \times 10^5$ |
| 4 | $9.6 \times 10^4$ | $3.5 \times 10^5$ |
| 8 | $8.2 \times 10^4$ | $5.8 \times 10^5$ |
| 12 | $5.0 \times 10^4$ | $3.9 \times 10^6$ |
| 16 | $6.6 \times 10^3$ | $1.7 \times 10^7$ |
| 20 | $3.4 \times 10^3$ | $6.8 \times 10^7$ |
| 24 | $2.2 \times 10^3$ | $9.5 \times 10^7$ |

By incorporating a spermicidal composition in the enzymatic foam, a contraceptive flexible foam pad is obtained.

EXAMPLE IV

This example illustrates an enzymatic pad which is self-contained with respect to oxidoreductase enzyme and corresponding oxidizable substrate for producing hydrogen peroxide in the presence of serum.

An enzymatic solution was prepared by dissolving, with stirring, glucose oxidase (5,000 IU) and glucose (5.0 gm) in methylene dichloride (50 ml). One millimeter of the enzymatic solution was added to a spun cotton pad similar to that described in Example I to effect solution deposition of the ingredients.

EXAMPLE V

This example illustrates an enzymatic pad which is self-contained with respect to oxidoreductase enzyme, oxidizable substrate, peroxidatic enzyme and oxidizable salt for producing an oxidized anionic bacterial inhibitor in the presence of serum.

An enzymatic solution was prepared by dissolving, with stirring, glucose oxidase (1,000 IU), glucose (10 gm), lactoperoxidase (500 IU), and potassium thiocyanate in methylene dichloride (50 ml). One millimeter of the enzymatic solution was added to a spun cotton pad similar to that described in Example I to effect solution deposition of the ingredients.

In view of the foregoing description and examples, it will become apparent to those of ordinary skill in the art that equivalent modifications thereof may be made without departing from the spirit and scope of this invention.

That which is claimed is:

1. An enzymatic substantially organic absorbent material for body contact application containing, per gram of material, from about 1.0 to about 1,000 International Units of serum-activated oxidoreductase enzyme for producing hydrogen peroxide upon contact of said material with serum.

2. The enzymatic material of claim 1 wherein the concentration of oxidoreductase enzyme is from about 10 to about 500 International Units.

3. The enzymatic material of claim 1 wherein the oxidoreductase enzyme is glucose oxidase.

4. The enzymatic material of claim 1 wherein the oxidoreductase enzyme is oxalate oxidase.

5. The enzymatic material of claim 1 which also contains from about 0.1 to about 10,000 International Units of peroxidatic peroxidase per gram of material.

6. The enzymatic material of claim 5 wherein the concentration of peroxidatic peroxidase is from about 10 to about 500 International Units per gram of material.

7. The enzymatic material of claim 5 wherein the peroxidatic peroxidase is lactoperoxidase.

8. The enzymatic material of claim 5 wherein the peroxidatic peroxidase is myeloperoxidase.

9. The enzymatic material of claim 1 which also contains, per gram of material, from about 0.03 to about 1.2 millimoles of substrate specific to oxidoreductase enzyme in said material for producing hydrogen peroxide upon contact of said material with serum.

10. The enzymatic material of claim 9 wherein the concentration of substrate is from about 0.06 to 0.6 millimoles per gram of material.

11. The enzymatic material of claim 9 wherein the substrate is glucose and the oxidoreductase enzyme is glucose oxidase.

12. The enzymatic material of claim 11 which also contains from about 0.1 to about 10,000 International Units of lactoperoxidase per gram of material.

13. The enzymatic material of claim 5 which also contains, per gram of material, from about 0.0001 to about 0.01 millimole of a metal salt of an oxygen accepting anion selected from the group consisting of thiocyanate, chloride and iodine or mixtures of such salts.

14. The enzymatic material of claim 13 wherein the concentration of the alkali metal salt is from about 0.001 to about 0.006 per gram of material.

15. The enzymatic material of claim 13 wherein the alkali metal salt is potassium thiocyanate.

16. The enzymatic material of claim 1 which also contains an aminoglucose selected from the group consisting of glucosamine, N-acetyl glucosamine and mixtures thereof in an amount from about 0.001 to about 0.002 millimole per gram of material.

17. The enzymatic material of claim 16 wherein the aminoglucose is present in an amount from about 0.0003 to about 0.001 millimole per gram of material.

18. The enzymatic material of claim 1 which also contains an effective amount of an enzymatic inhibitor specific to catalase.

19. The enzymatic material of claim 18 wherein the catalase inhibitor is an ascorbate salt in an amount from about 0.000001 to about 0.0001 millimole per gram of material.

20. An enzymatic substantially organic, absorbent fiber for conversion into enzymatic absorbent material for body contact application containing, per gram of fiber, from about 1.0 to about 1,000 International Units of serum-activated oxidoreductase enzyme for producing hydrogen peroxide upon contact with serum.

* * * * *